United States Patent
Czerny et al.

US010151004B2

(10) Patent No.: US 10,151,004 B2
(45) Date of Patent: Dec. 11, 2018

(54) **DETECTION METHOD FOR *MYCOBACTERIUM AVIUM* SPP. *PARATUBERCULOSIS***

(71) Applicant: Georg-August-Universitaet Goettingen Stiftung Oeffentlichen Rechts, Goettingen (DE)

(72) Inventors: Claus-Peter Czerny, Waake-Boesinghausen (DE); Pia Muenster, Goettingen (DE)

(73) Assignee: Georg-August-Universität Göttingen Stiftung Öffentlichen Rechts, Göttingen (DE)

( * ) Notice: Subject to any disclaimer, the term of this patent is extended or adjusted under 35 U.S.C. 154(b) by 509 days.

(21) Appl. No.: 14/397,029

(22) PCT Filed: Apr. 26, 2013

(86) PCT No.: PCT/EP2013/058701
§ 371 (c)(1),
(2) Date: Oct. 24, 2014

(87) PCT Pub. No.: WO2013/160434
PCT Pub. Date: Oct. 31, 2013

(65) Prior Publication Data
US 2015/0111206 A1    Apr. 23, 2015

(30) Foreign Application Priority Data
Apr. 27, 2012  (DE) .................. 10 2012 103 730

(51) Int. Cl.
*C12Q 1/68*    (2018.01)
*C12Q 1/689*    (2018.01)

(52) U.S. Cl.
CPC ....................... *C12Q 1/689* (2013.01)

(58) Field of Classification Search
None
See application file for complete search history.

(56) References Cited

U.S. PATENT DOCUMENTS 7,074,559 B2 *  7/2006  Kapur ................. C12Q 1/689
                                                                435/243

FOREIGN PATENT DOCUMENTS

| DE | 3854767 T2 | 9/1996 |
| EP | 1223225 A1 | 7/2002 |
| JP | 2001157584 A | 6/2001 |

OTHER PUBLICATIONS

Genbank Accession No. X16293—*Mycobacterium paratuberculosis* insertion element IS900 (submitted by Green et al. Aug 24, 1999, retrieved on Mar. 1, 2017 from http://www.ncbi.nlm.nih.gov/nuccore/X16293).*

Genbank Accession No. AF416985—*Mycobacterium avium* subsp. *paratuberculosis* insertion sequence IS900 putative transposase (p43) gene, complete cds (submitted by Willemsen et al. Sep. 6, 2001 retrieved on Mar. 1, 2017 from http://www.ncbi.nlm.nih.gov/nuccore/AF416985).*

Green EP, Tizard ML, Moss MT, Thompson J, Winterbourne DJ, McFadden JJ, Hermon-Taylor J. Sequence and characteristics of IS900, an insertion element identified in a human Crohn's disease isolate of *Mycobacterium paratuberculosis*. Nucleic Acids Res. Nov. 25, 1989; 17(22):9063-73.*

Herthnek D, Bölske G. New PCR systems to confirm real-time PCR detection of *Mycobacterium avium* subsp. *paratuberculosis*. BMC Microbiol. Oct. 4, 2006; 6:87 pp. 1 -8.*

Lowe T, Sharefkin J, Yang SQ, Dieffenbach CW. A computer program for selection of oligonucleotide primers for polymerase chain reactions. Nucleic Acids Res. Apr. 11, 1990; 18(7):1757-61.*

Rozen S, Skaletsky H: Primer3 on the WWW for general users and for biologist programmers. Methods Mol Biol 2000, 132:365-386.*

Münster P, Völkel I, Wemheuer W, Petschenka J, Wemheuer W, Steinbrunn C, Campe A, Schulz-Schaeffer WJ, Kreienbrock L, Czerny CP. Detection of *Mycobacterium avium* ssp. *paratuberculosis* in ileocaecal lymph nodes collected from elderly slaughter cows using a semi-nested IS900 polymerase chain reaction. Vet Microbiol. Dec. 29, 2011; 154(1-2):197-201.*

O'Mahony J, Hill C. Rapid real-time PCR assay for detection and quantitation of *Mycobacterium avium* subsp. *paratuberculosis* DNA in artificially contaminated milk. Appl Environ Microbiol. Aug. 2004; 70(8):4561-8.*

Bull et al., "A Novel Multi-Antigen Virally Vectored Vaccine Against *Mycobacterium avium* Subspecies *paratuberculosis*" PLoS One, Nov. 1, 2007, vol. 2, No. 11, e1229.

Logar et al., "Evaluation of Combined High-Efficiency DNA Extraction and Real-Time PCR for Detection of *Mycobacterium avium* Subsp. *paratuberculosis* in Subclinically Infected Dairy Cattle: Comparison with Faecal Culture, Milk Real-Time PCR and Milk ELISA", BMC Veterinary Research, 2012, vol. 8, No. 49, p. 1746-1761.

Muenster et al., "Detection of *Mycobacterium avium* ss. *paratuberculosis* in Ileocaecal Lymph Nodes Collected from Elderly Slaughter Cows Using a Semi-Nested IS900 Polymerase Chain Reaction", Veterinary Microbiology, 2011, vol. 154, p. 197-201.

Mahony et al., "Rapid Real-Time PCR Assay for Detection and Quantitation of *Mycobacterium avium* Subsp. *paratuberculosis* DNA in Artificially Contaminated Milk", Applied and Environmental Microbiology, Aug. 1, 2004, vol. 70, No. 8, p. 4561-4568.

(Continued)

*Primary Examiner* — Olayinka A Oyeyemi
(74) *Attorney, Agent, or Firm* — W & C, IP

(57) ABSTRACT

A method for specifically detecting and optionally for quantifying *Mycobacterium avium* ssp. *paratuberculosis* (MAP) in a sample of an individual is provided. For this purpose, the detection of the presence of the IS900 region in a sample is performed by nucleic acid amplification using specific oligonucleotides. In a further aspect, a test kit for specifically detecting MAP in a sample by amplification methods is also provided. Finally, specific oligonucleotides that are suitable for specifically detecting MAP are described.

6 Claims, 6 Drawing Sheets

Figure 1:
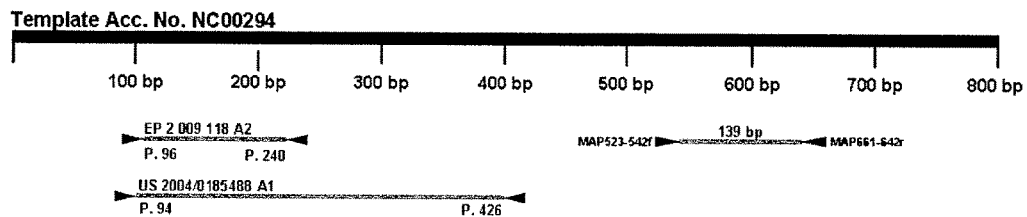

Specification includes a Sequence Listing.

(56) References Cited

OTHER PUBLICATIONS

Rodriguez-Lazaro et al., "Real-Time PCR-Based Methods for Detection of *Mycobacterium avium* Subsp. *paratuberculosis* in Water and Milk", Int J Food Microbiol, May 1, 2005, vol. 101, No. 1, p. 93-104.

Ravva et al., "Real-Time Quantitative PCR Detection of *Mycobacterium avium* Subsp. *paratuberculosis* and Differentiation from Other Mycobacteria Using SYBR Green and TaqMan Assays" J Microbiol Methods, Dec. 1, 2005, vol. 63, No. 3, p. 305-317.

Cook et al., Optimization of Methods for Detecting *Mycobacterium avium* Subsp. *paratuberculosis* in Environmental Samples Using Quantitative, Real-Time PCR J Microbiol Methods, Apr. 1, 2007, vol. 69, No. 1, p. 154-160.

Kawaji et al., "Detection of *Mycobacterium avium* Subsp. *paratuberculosis* in Ovine Faeces by Direct Quantitative PCR has Similar or Greater Sensitivity Compared to Radiometric Culture", Vet Microbiol, Nov. 15, 2007, vol. 125, No. 1-2, p. 36-48.

Muenster, "Epidemiological Investigations on the Occurrence of *Mycobacterium avium* Subspecies *paratuberculosis* in Different Matrices from Cattle and Zoo Animals by IS900 Polymerase Chain Reaction Assays" PhD Dissertation; Georg-August-University Goettingen, Mar. 1, 2012, Whole Document.

\* cited by examiner

SEQUENCE LISTING

<160> NUMBER OF SEQ ID NOS: 4

<210> SEQ ID NO 1
<211> LENGTH: 20
<212> TYPE: DNA
<213> ORGANISM: artificial

```
<220> FEATURE:
<223> OTHER INFORMATION: Synthetic oligonucleotide

<400> SEQUENCE: 1
taccgcggcg aaggcaagac                                                  20

<210> SEQ ID NO 2
<211> LENGTH: 20
<212> TYPE: DNA
<213> ORGANISM: artificial
<220> FEATURE:
<223> OTHER INFORMATION: Synthetic oligonucleotide

<400> SEQUENCE: 2
cggaacgtcg gctggtcagg                                                  20

<210> SEQ ID NO 3
<211> LENGTH: 20
<212> TYPE: DNA
<213> ORGANISM: artificial
<220> FEATURE:
<223> OTHER INFORMATION: Synthetic oligonucleotide

<400> SEQUENCE: 3
atgacatcgc agtcgagctg                                                  20

<210> SEQ ID NO 4
<211> LENGTH: 1453
<212> TYPE: DNA
<213> ORGANISM: Mycobacterium avium ssp. paratuberculosis

<400> SEQUENCE: 4
tccttacctt tcttgaaggg tgttcggggc cgtcggcctt aggcttcgaa ttgcccaggg      60
acgtcgggta tggctttcat gtggttgctg tgttggatgg ccgaaggaga ttggccgccc     120
ggcgtcccgc gacgactcga ccgctaattg agagatgcga ttggatcgct gtgtaaggac     180
acgtcggcgt ggtcgtctgc tgggttgatc tggacaatga cggttacgga ggtggttgtg     240
gcacaacctg tctgggcggg cgtggacgcc ggtaaggccg accattactg catggttatt     300
aacgacgacg cgcagcgatt gctctcgcag cgggtggcca acgacgaggc cgcgctgctg     360
gagttgattg cggcggtgac gacgttggcc gatggaggcg aggtcacgtg ggcgatcgac     420
ctcaacgccg gcggcgccgc gttgctgatc gccttgctca tcgctgccgg gcagcggctg     480
ctttatattc ccgggcgcac ggtccatcac gccgcgggta gttaccgcgg cgaaggcaag     540
accgacgcca aagacgctgc gatcatcgcc gatcaggccc ggatgcgcca cgacttgcag     600
cctctgcgcg ccggcgatga catcgcagtc gagctgcgca tcctgaccag ccgacgttcc     660
gatctggtgg ctgatcggac ccgggcgatc gaaccgaatg cgcgcccagc tgctggaata     720
ctttcggcgc tggaacgcgc cttcgactac aacaagagcc gtgccgcgct gatcctgctt     780
actggctacc aaactcccga cgcgctgcgc agcgccggtg gcgctcgagt agccgcgttc     840
ttgcgtaaac gcaaggcccg caacgccgat accgtcgcag ccaccgcgct gcaggccgct     900
aacgcccaac acagcatcgt gcccggccaa caactggcgg ccactgtggt ggcccgcctg     960
gccaaggagg tgatggccct cgacaccgaa atcggcgaca ccgacgcgat gatcgaggag    1020
cgatttcgcc gccaccgcca cgccgaaatc atcctgagca tgcccggatt cggcgtcatc    1080
ctgggcgctg agttcctcgc cgccaccggc ggggacatgg ccgcattcgc ctccgccgac    1140
cgcctcgccg gcgtcgccgg cctggcgccg gtaccacgag attccggccg catcagcgga    1200
```

```
aacctcaaac gcccccgacg ctacgaccgg cgcctgctgc gcgcctgcta cctgtcggcc    1260
ttggtcagca tccgcaccga cccctcctcg cgcacctact acgaccgaaa acgcaccgaa    1320
ggaaaacgcc acacccaagc cgtcctcgcc ctggcccgcc gccgcctcaa cgtcctgtgg    1380
gccatgctgc gcgaccacgc tgtctaccac cccgcaacca ctaccgcggc ggcttgacaa    1440
cgtcattgag aat                                                       1453
```

DETECTION METHOD FOR MYCOBACTERIUM AVIUM SPP. PARATUBERCULOSIS

The present application relates to a method for specific detection and optionally quantification of *Mycobacterium avium* spp. *paratuberculosis* (MAP) in a sample from an individual. For this, according to the method according to the invention, the detection of the presence of the IS900 region in a sample is effected by means of a nucleic acid amplification and specific oligonucleotides. In a further aspect, a test kit for specific detection of MAP in a sample by amplification methods is provided herein. Finally, specific oligonucleotides which are suitable for specific detection of MAP are disclosed.

PRIOR ART

*Mycobacterium avium* is a *mycobacterium* species which has a great variety of hosts. On the one hand, *Mycobacterium avium* can cause tuberculosis in poultry, and on the other, also occurs as a pathogen in man and other mammals. One species of this is *Mycobacterium avium* spp. *paratuberculosis* (MAP), an obligate pathogenic bacterium of the genus *Mycobacterium*. MAP is regarded as the cause of *paratuberculosis* (Johne's disease), a disease which occurs in ruminants in particular. It has also been possible to detect the subspecies MAP in other animal species apart from ruminants and man, particularly in wild animals, in, inter alia, hares, birds, wild cats, raccoons and rats. Moreover, there is discussion of possible involvement of this pathogen in the clinical picture "Crohn's disease" in man.

The pathogen MAP has been known since the start of the 19$^{th}$ century as the causative agent of *paratuberculosis*. *Paratuberculosis* is a chronic intestinal disease which leads to continuing weight loss over a period of weeks. In the final stage, this disease has a fatal outcome. Adult domestic ruminants such as cattle, sheep and goats, but also wild ruminants and zoo animals are predominantly infected. Usually the transmission of the pathogen mainly takes place in newborn calves and calves up to the age of 6 months. Here the infection mostly occurs insidiously and goes unrecognized by the oral-fecal route, and even the colostral milk of infected cows can contain the pathogen. After a latency period of several years with irregular and uncontrollable pathogen excretion, the disease typically first appears in older cows. At present there is no therapy. In the past, vaccines have shown dubious success, so that they are not at present used in Germany. Commonly, the purchase of subclinically or persistently infected animals is responsible for new infections within a herd. It is precisely the clinically unremarkable carriers and unrecognized excreters that are the most important cause of permanently ongoing stock infections. It is precisely because of the wide distribution of *paratuberculosis* and economic losses that improved diagnostic methods and the development of control programs are currently being demanded. In Germany, *paratuberculosis* is notifiable under § 78a Art. 2 of the Infectious Animal Diseases Law.

The diagnosis of *paratuberculosis* is a significant element in the control and early recognition of *paratuberculosis*. There are already various test methods and diagnostic methods which rely on antibody-based tests for example. However, one problem with the commercially available tests is the inadequate sensitivity and inadequate specificity. Moreover, antibody-based tests are unsuitable since serologically negative excreters can remain in the herds owing to the inadequate sensitivity of these tests and can thus further spread the disease.

In order to be able to implement an effective eradication program in the future, reliable pathogen detection methods are necessary. Molecular biological methods, in particular methods based on nucleic acid amplification have often been discussed. In particular, molecular biological methods based on the polymerase chain reaction (PCR) are considered very promising. The PCR is a rapid and reliable method for confirming MAP DNA in suspect samples. In this, the insertion sequence IS900, but also regions of ISMav2, hspX and F57, have been identified as particularly suitable regions of the MAP genome. The insertion element IS900 in particular stands out as a suitable region for molecular diagnosis, in particular by PCR methods.

IS900 is a 1451 bp fragment which has 17 copies within the genome of the reference strain MAP-K10. Because of this high copy number, higher sensitivity in the detection method can be achieved and makes IS900 a suitable target region. Conventional and real-time PCR for the detection of MAP based on the target sequence IS900 have been described.

Thus DE102007015775A1 contains oligonucleotides suitable for the specific detection of MAP. Further, this document discloses corresponding methods and test kits for the detection of MAP. From EP 2 009 118 A2, a method for detection and quantification of MAP on the basis of IS900 and F57 specific primers is known.

However, as before, the methods described there still suffer from inadequate sensitivity at high specificity.

Bull et al., 2007, Plos One, 11, e1229, describes a real-time PCR assay for detecting MAP. Münster P., et al., 2011, Vet Microbiol, 154(1-2), 197-201, discloses a semi-rested PCR (snPCR) for detecting MAP. A high sensitivity is described. However, an snPCR requires the performance of two PCR runs. snPCR is known as a method in which there is a high contamination risk and is therefore not suitable for routine use with a high sample throughput.

It is however necessary to detect infected individuals with high sensitivity and great specificity in order to conduct an appropriate eradication program. In particular, this method should also be operable in biological samples such as fecal, organ, milk and tissue samples without having to perform extensive prior culturing, which requires up to 16 weeks, or processing steps.

In addition, this method should be suitable to permit appropriate automation. The methods described in the state of the art do not permit this.

DESCRIPTION OF THE INVENTION

In a first aspect, the present application relates to a method for specific detection or quantification of *Mycobacterium avium* spp. *paratuberculosis* (MAP) in a sample from an individual. For this, the method according to the invention comprises the step of detecting the IS900 region of an MAP genome in a sample by nucleic acid amplification, wherein this amplification is performed with the specific oligonucleotides respectively consisting of at least 15 successive nucleotides of the sequences according to Seq. ID No. 1 and Seq. ID No. 2, and detection of the IS900 region of at least one MAP genome indicates the presence of MAP in the sample.

It was then discovered that the specific oligonucleotides as used here, namely the oligonucleotides which respectively have at least 15 consecutive nucleotides of the sequences according to Seq. ID No. 1 and Seq. ID No. 2, allow outstanding specificity and sensitivity towards MAP in diagnostic methods on the basis of one nucleic acid amplification.

Here it is preferable that the oligonucleotides according to Seq. ID No. 1 and/or Seq. ID No. 2 independently of one another have at least 16, such as 17 or 18 consecutive, and in particular, at least 19 nucleotides of these two sequences. It is more preferable that at least one of the specific oligonucleotides according to Seq. ID No. 1 and/or Seq. ID No. 2 has at least 11, 12, 13, 14, 15, in particular at least 16, 17, 18, 19 or all nucleotides of said sequences. It is clear that embodiments are also included wherein one oligonucleotide for example has at least 18 nucleotides of the sequence according to Seq. ID No. 1 and at least 19 nucleotides of the sequence according to Seq. ID No. 2. Every variation is included in the scope of this invention.

The nucleic acid amplification method is preferably a polymerase chain reaction (PCR). This can in particular be a real-time PCR. The PCR, for example in the form of a real-time PCR, is in particular a quantitative PCR.

In contrast to known methods which are also based on a PCR, with the oligonucleotides according to the invention as the primer pair, it is now possible to obtain meaningful results in one amplification cycle. Previously known methods often rely on the so-called "nested" or "semi-nested" PCR" methods. In these, the amplification takes place in two steps, i.e. the method takes longer and is more expensive than a single step method. Further advantages of the real-time PCR are the possibility of quantification of the MAP DNA, rapid implementation with low contamination risk and the guarantee of high sensitivity and specificity.

It is especially preferable that in the nucleic acid amplification such as the PCR, in particular the real-time PCR, and especially preferably in the quantitative PCR, the detection of the IS900 region is effected by means of a nucleic acid probe. This nucleic acid probe is an oligonucleotide usually marked with a label or marker which hybridizes to the IS900 region of the MAP genome and/or to a nucleic acid complementary to the IS900 region of the MAP genome.

Herein, hybridization is understood to mean that a nucleic acid molecule such as the nucleic acid probe attaches itself to at least one other nucleic acid molecule, here an amplified gene fragment, wherein in the attachment region the two individual strands of the nucleic acids are essentially fully complementary. Triple helices can also form between the nucleic acid probe and existing double stranded DNA. Known hybridization methods are known to those skilled in the art. In particular, the hybridizing regions are at least 70% complementary, such as at least 75%, in particular at least 80%, preferably at least 90%, such as at least 95%, in particular at least 99%, such as fully complementary.

In a preferred embodiment, the nucleic acid is an oligonucleotide with at least 15 consecutive nucleotides according to Seq. ID No. 3. It is preferable that the probe is one with at least 16, 17 or 18 consecutive nucleotides according to Seq. ID No. 3, preferably with 19 nucleotides, such as the sequence of Seq. ID No. 3 itself with 20 nucleotides.

Here, the probe is marked in a usual way with a label or marker which allows simple detection with known methods. Usual labels or markers are known to those skilled in the art, such as fluorescent dyes, for example FAM (5 or 6 carboxyfluorescein), VIC, NID, fluorescein, fluorescein isothiocyanate (FITC), 6-carboxy-2',4',7',4,7-hexa-chlorofluorescein (HEX), cyanine dyes such as Cy3, Cy5, etc., rhodamine dyes, phenanthridine dyes and other dyes well known to those skilled in the art. Particularly suitable for probe detection are FAM and black hole quencher-1 (BHQ1).

For the particular nucleic acid amplification protocol, such as PCR, real-time PCR, and in particular for quantitative PCR, the suitable dyes in combination with the suitable amplification systems are known to those skilled in the art.

In real-time PCR, alternatively inactive, for example quenched, fluorescent dyes which are activated by DNA production are added. Usual dyes which can intercalate with the synthesized double strand DNA are for example ethidium bromide or SYBR green. In the utilization of the TaqMan system for nucleic acid amplification, the nucleic acid probes are those which are detectable by hydrolysis, for example by determination of the corresponding fluorescence. Further suitable systems on the basis and for example LightCycler probes, FRET probes, molecular beacons or scorpion primers are known to those skilled in the art. The nucleic acid amplification method is especially preferably a quantitative real-time PCR with primers according to Seq. ID No. 1 and Seq. ID No. 2 and a nucleic acid probe according to Seq. ID No. 3.

In the method according to the invention and also in the test kits according to the invention, appropriate controls can also be present. These controls include controls for amplification and/or controls for purification. These controls can for example be present in the sample itself or be performed in a parallel preparation. Thus, for example the probe in the real-time PCR can be equipped with a quenched dye such as FAM. At the same time, the probe is equipped with a second marker which can be detected in a different region from the quenched dye, for example emits light in a different region, and is not quenched. Checking of the PCR is thereby possible. In addition, a positive control such as β-actin can be amplified in the sample or parallel thereto. Detection thereof is effected with a marker which is different from the first and second markers, for example a Cy5 dye. Thereby checking of the reaction is possible and enables improvement of the validity of the method. For the amplification control, which excludes the inhibitory effect of a clinical sample, a second fluorescent dye (for example HEX, measured at 533-580 nm) for the probe can be integrated.

Further, for quantification, suitable positive controls for MAP can be used in predetermined concentrations in parallel preparations. The appropriate experimental preparations are known to those skilled in the art.

The nucleic acid amplification is preferably effected from a sample from an individual. Here the sample subjected to nucleic acid amplification can be a sample which consists of a large number of pooled samples in order to thus enable effective testing for MAP. Usually a pooled sample can be a mixture of for example 10 to 20 individual samples from different individuals. Alternatively, the sample is a sample from a single individual.

The expression individual is herein understood to mean an individual selected from ruminants, in particular cattle, sheep and goats or also wild ruminants, such as zebras etc. Herein it can also be for example zoo animals. People also fall within the expression individual. Thus the method can for example be used to test for an infection with MAP in a person, for example in connection with the diagnosis of Crohn's disease.

The sample itself can be a selected from a fecal, milk, blood, semen, tissue or organ sample. Alternatively, environmental samples, for example plant-based samples or samples from biogas installations and lakes/rivers are also possible.

The sample is preferably a fecal sample or a milk sample from a ruminant, in particular a bovine.

Also, according to the invention the sample can be processed by suitable methods. Usual methods include processing of the sample. Suitable methods are known to those skilled in the art. In particular, the processing can be effected by means of known DNA extraction methods. These include the use of known kits based on surfactants and salts. Furthermore, mechanical DNA extraction methods are possible, including processing using homogenizers, etc. In particular, methods which include the use of surfactants for extraction are suitable.

In a further aspect, the present invention relates to test kits for specific detection of MAP in a sample by amplification methods, in particular by PCR. The test kits include oligonucleotides for amplification of the MAP IS900 region with at least 15 consecutive nucleotides according to Seq. ID Nos. 1 and 2 respectively. This test kit is preferably one for PCR nucleic acid amplification, in particular one for real-time PCR. In an especially preferred embodiment, the test kit is one suitable for quantitative PCR, such as quantitative real-time PCR. In one embodiment, the test kit further includes an oligonucleotide with at least 15 consecutive nucleotides of the nucleic acid probe according to Seq. ID No. 3. This test kit is particularly suitable for quantitative analysis, for example on the basis of the TaqMan PCR. The test kit according to the invention can further contain further components for performing the nucleic acid amplification, in particular the necessary enzymes, nucleotides and buffers. Moreover, a positive control can also preferably be included therewith and/or directions for performing the method according to the invention.

Finally, the test kit can contain appropriate reagents and means which are suitable for the extraction of genomic DNA from samples, in particular fecal, milk, blood, semen, organ, tissue and environmental samples, and/or means for performing the PCR, in particular real-time PCR.

Suitable reagents and means are known to those skilled in the art.

Finally, the application relates to oligonucleotides for specific detection and, optionally, quantification of MAP in a sample from an individual, wherein at least 15 consecutive nucleotides of the sequence Seq. ID No. 1 and at least 15 consecutive nucleotides of the sequence Seq. ID No. 2 are present and, optionally, at least 15 consecutive nucleotides of the sequence Seq. ID No. 3.

These oligonucleotides are in particular suitable in the use for specific detection and optionally for quantification of MAP in particular by means of quantitative real-time PCR. The oligonucleotides according to the invention are those mentioned above.

The invention is explained in more detail below by means of examples, without being restricted to them.

Practical Example

To check the specificity of the primers according to the invention ($MAP_{523-542f}/MAP_{661-642r}$) and the TaqMan probe ($MAP_{617-636p}$) according to table 1, 14 *mycobacterium* species and 14 non-*mycobacterium* species which often occur in agriculture and in the environment were tested both in the classical and also the real-time PCR and the specificity was confirmed (table 2). FIG. 1 shows the position of the primers according to the invention to the primers from the state of the art.

TABLE 1

Nucleic acid sequences of the primers and TaqMan probe for detecting MAP DNA in real-time PCR

| Primer/probe | Sequence (5'-3') | Location/Seq. ID No. * |
|---|---|---|
| $MAP_{523-542f}$ | TACCGCGGCGAAGGCAAGAC | 523-542/1 |
| $MAP_{661-642r}$ | CGGAACGTCGGCTGGTCAGG | 661-642/2 |
| $MAP_{617-636p}$ | ATGACATCGCAGTCGAGCTG | 617-636/3 |

* According to the published IS900 sequence MAP K-10 (GenBank: AF416985), Seq. ID No. 4

TABLE 2

Reference strains used for specificity testing of the Taq-Man real-time PCR

| Bacterial species | Name/source |
|---|---|
| *Mycobacterium* species | |
| *M. avium* ssp. *paratuberculosis* | ATCC 19698 |
| *M. avium* ssp. *avium* | ATCC 15769 |
| *M. avium* ssp. *avium* | ATCC 19421 |
| *M. avium* ssp. *avium* | ATCC 25291 |
| *M. avium* ssp. *silvaticum* | ATCC 49884 |
| *M. bovis* | ATCC 27289 |
| *M. fortuitum* | ATCC 6841 |
| *M. gordonae* | ATCC 14470 |
| *M. intracellulare* | ATCC 13950 |
| *M. kansasii* | ATCC 12478 |
| *M. marinum* | ATCC 927 |
| *M. phlei* | ATCC 354 |
| *M. scrofulaceum* | ATCC 19981 |
| *M. smegmatis* | ATCC 19420 |
| Other bacterial species | |
| *Campylobacter jejuni* | ATCC 33560 |
| *Clostridium perfringens* | Cattle |
| *Clostridium sordelli* | Cattle |
| *Escherichia coli* 0101:K28 | Cattle |
| *Escherichia coli* 0149:K91 | Swine |
| *Escherichia coli* 0157:H7 | ATCC 700927 |
| *Enterococcus faecalis* | ATCC 19433 |
| *Enterococcus hirae* | ATCC 10541 |
| *Rhodococcus equi* | ATCC 25694 |
| *Salmonella cholerasuis* | Cattle |
| *Salmonella thyphimurium* | Cattle |
| *Staphylococcus aureus* | Cattle |
| *Streptococcus dysgalactiae* | Cattle |
| *Streptococcus uberis* | Cattle |

The DNA of the reference strains used was extracted from cultures by means of the QIAmp Blood Kit (Quiagen, Hilden, Germany) and assayed by means of Nano-Drop® (ND-1000 Spectrophotometer, peQLab Biotechnologie GmbH, Erlangen). The DNA was adjusted to 1 ng/µg. The species-specific DNA of the reference strains was confirmed by the use of published PCR methods. Sterile distilled water was used as the negative control.

In all cases, the PCR products to be expected from the particular genus-specific PCR could clearly be recognized on the agarose gel.

Figure 2:
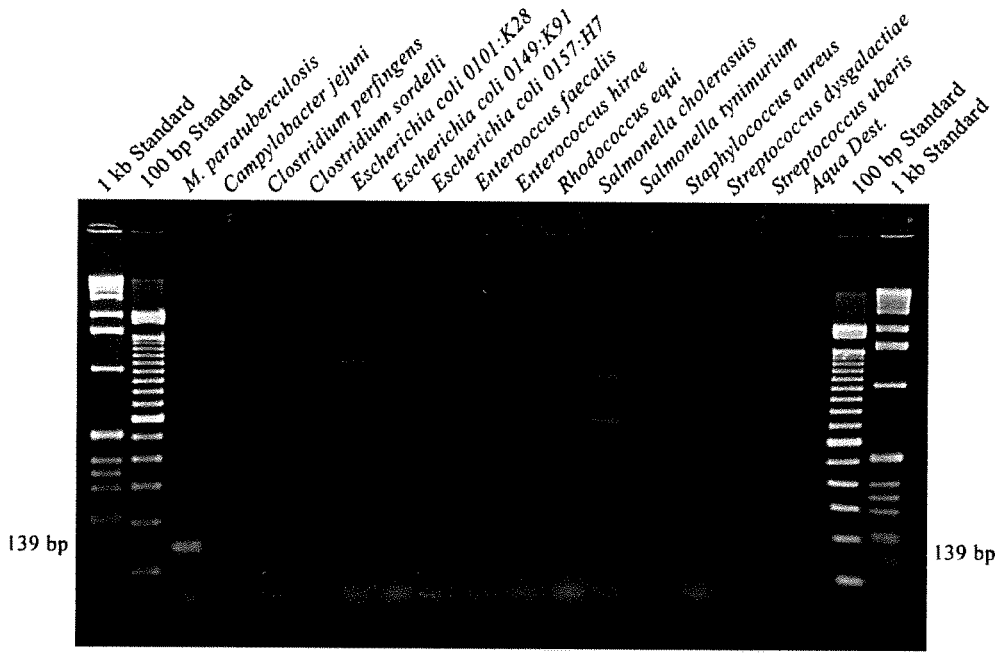

To clarify their specificity, both primers ($MAP_{523-542f}/MAP_{661-642r}$) were tested for cross-reactivity with other bacterial species in the classical PCR (FIG. 2). For the preparation of the PCR, "Ready-To-Go®" PCR "beads" (Amersham Pharmacia Biotech Europe, Freiburg) were used. Reaction preparations and conditions for the PCR were as follows:

| | |
|---|---|
| Ready-To-Go™ PCR beads | 1 bead |
| Dist. Water | 21 µl |
| Primer MAP-for (10 pmol/µl) | 1 µl |
| Primer MAP-rev (10 pmol/µl) | 1 µl |
| Template | 2 µl |

The PCR is preceded by a denaturation step at 95° C. for 4 mins.

| | | |
|---|---|---|
| Denaturation: | 95° C., | 30 secs |
| Annealing: | 58-70° C., | 30 secs |
| Elongation: | 72° C., | 60 secs |

Prolongation of the elongation at 72° C. for 7 mins constitutes the end of the PCR.

The 139 bp PCR products to be expected could clearly be recognized on the agarose gel and only with the MAP DNA sample (ATCC 19698). Amplification products in the 139 bp region were not observed with other bacterial species (n=14). Hence the primers used (MAP$_{523-542f}$/MAP$_{661-642r}$) can be regarded as MAP-specific.

In addition, the specificity was confirmed by sequencing the 139 bp product. For this, the PCR products were cloned into the plasmid vector pCR® 2.1-TOPO® (Invitrogen, Groningen, Netherlands), proliferated in E. coli bacteria and purified with the Wizard® Plus SV Minipreps Purification System (Promega, Mannheim). The nucleotide sequences were compared with the sequence of the MAP K-10 reference strain (Accession No. AE16958) by means of MegAlign. A total of 15 clones were sequenced and evaluated in both directions. The IS900 sequences of the amplification products agreed 100% with the published bovine MAP K-10 sequence.

After the specificity of the primers (MAP$_{523-542f}$/MAP$_{661-642r}$) had been checked in the classical PCR on the basis of reference strains (n=14) the specificity of the probe (MAP$_{617-636p}$) had to be confirmed in combination with the primers in the real-time PCR. As the negative control, sterile distilled water was used. The reaction preparation and reaction conditions for the real-time PCR with the TaqMan probe on the LightCycler™ 480 (Roche Diagnostics, Mannheim) were as follows:

| | | |
|---|---|---|
| LightCycler™ 480 Master | 10 µl | |
| Primer MAP-for (10 pmol/µl) | 0.5 µl | |
| Primer MAP-rev (10 pmol/µl) | 0.5 µl | |
| Probe (10 pmol/µl) | 1 µl | |
| Dist. Water | 3 µl | |
| Template | 5 µl | |
| 95° C. | 10 mins | |
| 95° C. | 15 secs | |
| 60° C. | 30 secs | 45 cycles |
| 72° C. | 35 secs | |

Figure 3:
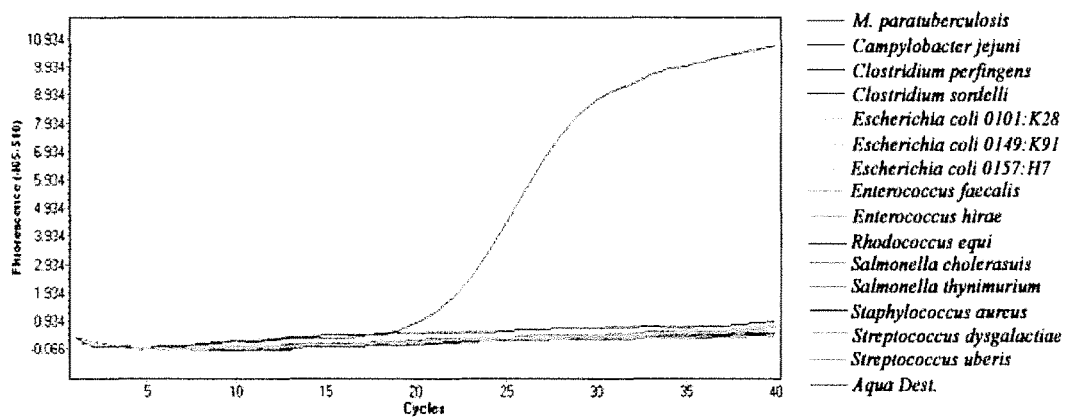

FIG. 3 shows the detection of MAP by means of the TaqMan probe (MAP$_{617-636p}$).

The MAP specificity of the primers (MAP$_{523-542f}$/MAP$_{661-642r}$) and the TaqMan probe (MAP$_{617-636p}$) could be adequately substantiated. A signal was only visible with the reference strain MAP (ATCC 19698). The reaction of the other bacterial species was comparable with the negative control.

For further clarification of the specificity, the primers (MAP$_{523-542f}$/MAP$_{661-642r}$) and the TaqMan probe (MAP$_{617-636p}$) were tested for cross-reactivity with other mycobacterium species (n=13).

The DNA of the mycobacterium reference strains used was purified from cultures as described above and assayed by means of Nano-Drop®. The DNA was adjusted to a concentration of 1 ng/µl. The species-specific DNA of the reference strains was confirmed by use of a published "multiplex" PCR method (Shin et al., 2010, Journal of Clinical Microbiology 48 (11), 4057-4062). As the negative control, sterile distilled water was used. Reaction preparation and reaction conditions were as stated in the literature.

Figure 4:
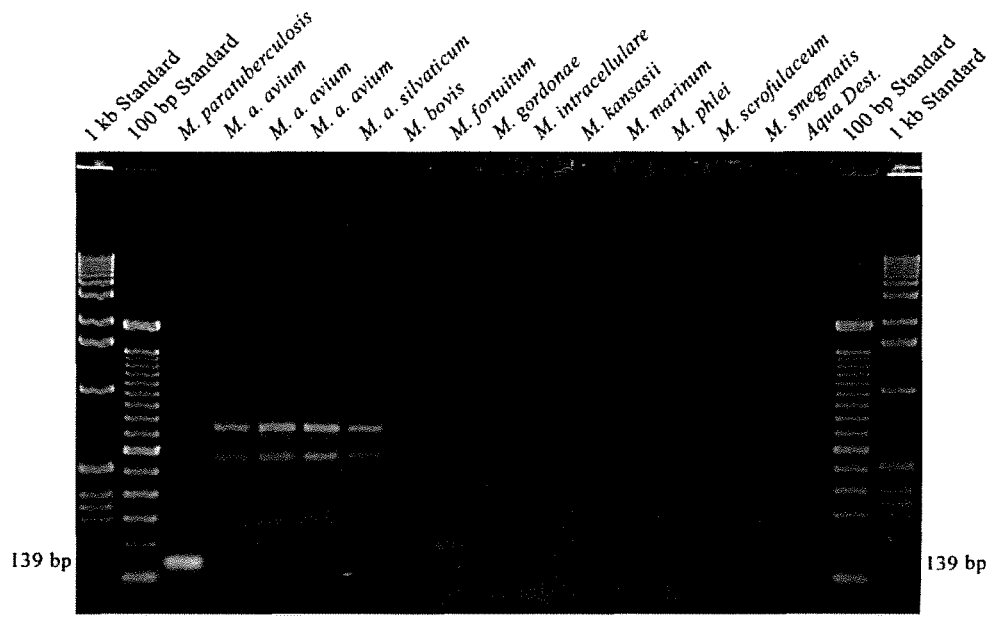

The PCR products to be expected from the particular mycobacterium species could be clearly recognized on the agarose gel. For further clarification of the specificity of the primers (MAP$_{523-542f}$/MAP$_{661-642r}$), these were tested for cross-reactivity with other mycobacterium species in the classical PCR (FIG. 4).

The 139 bp PCR products to be expected could be clearly recognized on the agarose gel only in the case of MAP DNA (ATCC 19698). Amplification products in the 139 bp region did not occur with other mycobacterium species (n=13). Hence the primers used (MAP$_{523-542f}$/MAP$_{661-642r}$) can be regarded as MAP-specific relative to other mycobacterium species.

After the specificity of the primers (MAP$_{523-542f}$/MAP$_{661-642r}$) had been checked in the classical PCR on the basis of mycobacterium reference strains (n=13) the specificity of the probe (MAP$_{617-636p}$) had to be confirmed in combination with the primers in the real-time PCR. As the negative control, sterile distilled water was used. The reaction preparation and reaction conditions for the real-time PCR with the TaqMan probe on the LightCycler™ 480 were as already defined above.

The MAP specificity of the primers (MAP$_{523-542f}$/MAP$_{661-642r}$) and the TaqMan probe (MAP$_{617-636p}$) could also be adequately substantiated against other mycobacterium species. A signal was only visible with the reference strain MAP (ATCC 19698). The reaction of the other mycobacterium strains was comparable with the negative control.

Figure 5:
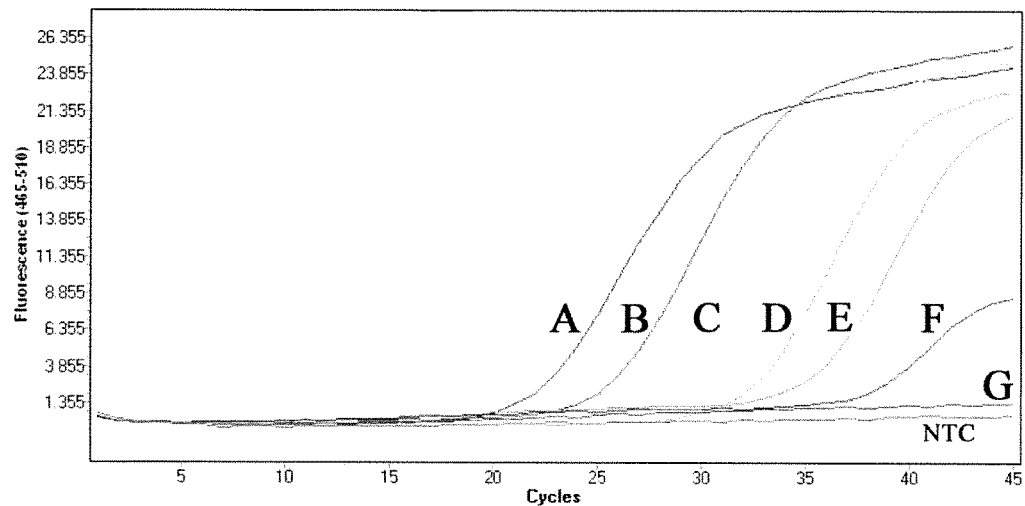

The detection limit or sensitivity of the TaqMan real-time PCR developed was determined by a titration series from 1 ng/µl to 1 fg/µl plasmid DNA and MAP DNA (ATCC 19698) from culture (FIG. 5).

For the preparation of plasmid DNA, PCR products (139 bp) were cloned and purified as described above. Next, the nucleic acid content of the plasmid DNA was determined by means of NanoDrop® and a dilution series from 1 ng/µl to 1 fg/µl wash prepared.

On use of MAP DNA prepared in culture, a detection limit of 10 fg/µl was achieved. The genome of MAP has a length of $4.7 \times 10^6$ bp (Cocito et al., 1994, Clinical Microbiology Reviews 7 (3), 328-345). Using the Avogadro constant $6.022 \times 10^{23}$ mol$^{-1}$ and the molecular weight of one base pair of 660 g×mol$^{-1}$, it could be calculated that 5.15 fg corresponds to one genome unit (Münster et al., 2011, Veterinary Microbiology 154, 197-201; Münster et al., 2012). According to this calculation, the detection limit at 10 fg/µl was ca. 2 genome units.

After checking of the specificity and sensitivity, the efficiency of the real-time PCR was tested. The efficiency is a quality characteristic of a quantitative real-time PCR. By comparison of the Cp values obtained and the MAP DNA concentration, a standard curve was created. A standard curve states the logarithmic concentration of the isolated DNA of the pathogen at the respective dilution stages. The slope of the straight line was −3.42±0.23, the error 0.04±0.02 and the efficiency was 1.97±0.08 (evaluation by "$2^{nd}$ derivative maximum" method). Thus the linear standard curve was found to be suitable for quantitative use of the TaqMan real-time PCR.

Figure 6:
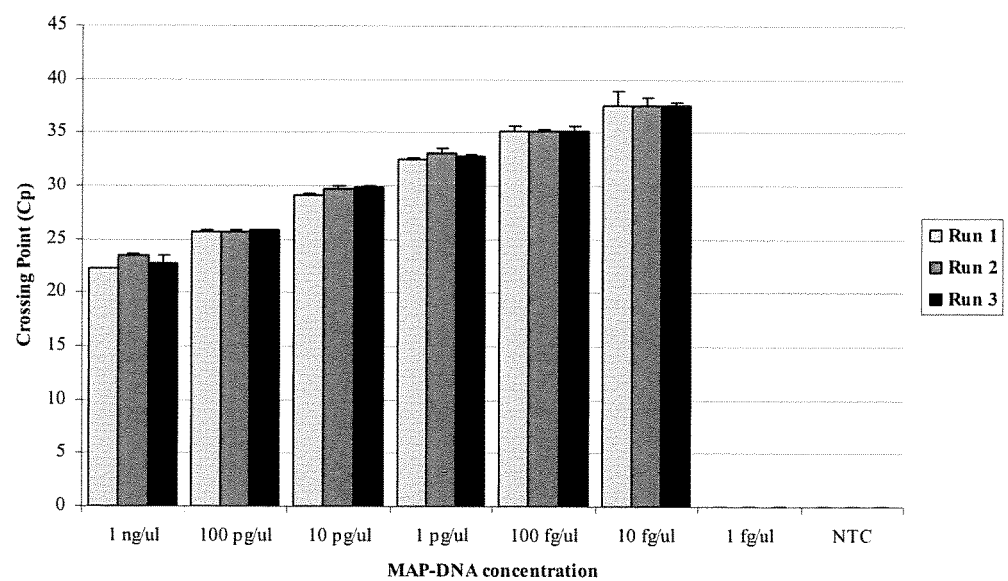
Figure 7:
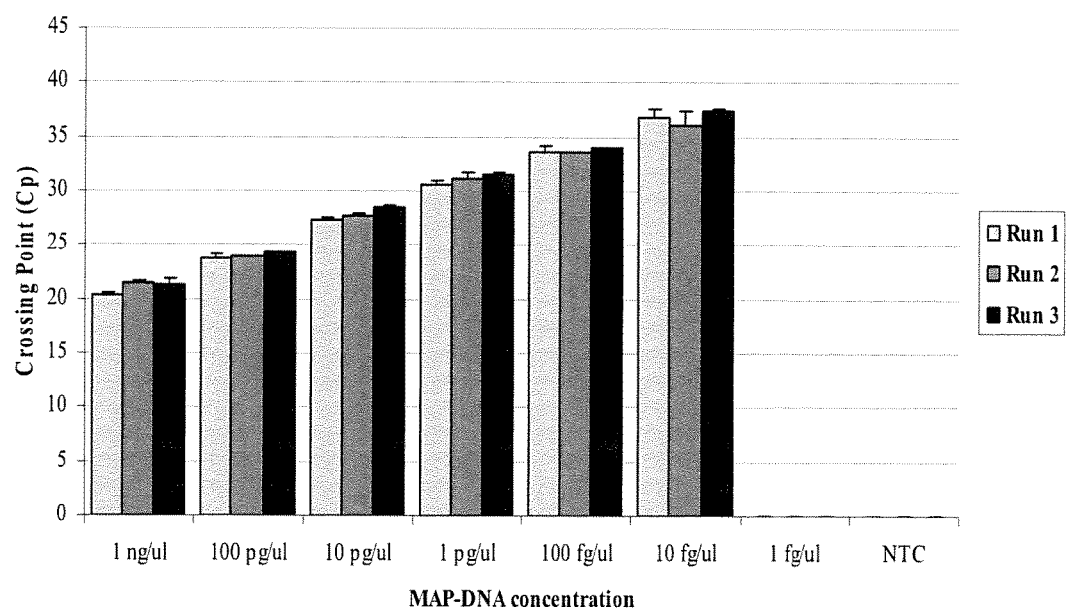

The reproducibility of the real-time PCR was determined from 9 repetitions on the LightCycler™ 480 (3×3 runs) and assessed by the "$2^{nd}$ derivative method" and the "fit point" method. For visualization, the respective mean value and the standard deviation of the "crossing points" (Cp), i.e. the cycle number at which the fluorescence first rises significantly above the background fluorescence, were calculated and represented as a bar diagram (FIGS. 6 and 7).

It could be shown that the real-time PCR yielded reproducible results. All nine repetitions yielded similar mean values for the Cp values, while the standard deviation was statistically low (maximum±0.73).

An evaluation by the "fit point" method also obtained reproducible results with a constant sensitivity of 10 fg/µl.

To check the quantifiability of the TaqMan real-time PCR and to illustrate the agreement of the calculated with the known MAP DNA concentration, these were calculated and compared in table 3. DNA concentrations were calculated both with the "$2^{nd}$ derivative maximum" and also with the "fit point" method. In the latter, the "noise band" was manually set at 6.00 and the "treshold" at 3.00.

TABLE 3

Quantification of MAP DNA from culture in $\log_{10}$ dilution stages by TaqMan real-time PCR on the basis of 9 repetitions (3 × 3 runs). Evaluation was by "$2^{nd}$ derivative maximum" and "fit point" methods.

| Sample | Known conc. | $2^{nd}$ Derivative maximum | | Fit point | |
|---|---|---|---|---|---|
| | | Calculated conc. | Cp value | Calculated conc. | Cp value |
| 1 ng/µl | $10^{-9}$ | $9.17 \times 10^{-10}$ | 22.79 ± 0.65 | $1.10 \times 10^{-9}$ | 21.00 ± 0.62 |
| 100 pg/µl | $10^{-10}$ | $1.25 \times 10^{-10}$ | 25.76 ± 0.07 | $1.33 \times 10^{-10}$ | 23.94 ± 0.34 |
| 10 pg/µl | $10^{-11}$ | $9.12 \times 10^{-12}$ | 29.61 ± 0.38 | $7.62 \times 10^{-12}$ | 27.88 ± 0.52 |
| 1 pg/µl | $10^{-12}$ | $8.19 \times 10^{-13}$ | 32.82 ± 0.39 | $7.46 \times 10^{-13}$ | 31.11 ± 0.54 |
| 100 fg/µl | $10^{-13}$ | $1.29 \times 10^{-13}$ | 35.18 ± 0.36 | $1.14 \times 10^{-13}$ | 33.73 ± 0.35 |
| 10 fg/µl | $10^{-14}$ | $1.05 \times 10^{-14}$ | 37.61 ± 0.73 | $1.26 \times 10^{-14}$ | 36.80 ± 0.94 |
| 1 fg/µl | $10^{-15}$ | — | — | — | — |
| NTC | — | — | — | — | — |

Similar values for the known and calculated DNA concentrations indicated the basic quantifiability of MAP DNA by TaqMan real-time PCR. Even when the reaction preparations of the dilution series of MAP DNA were evaluated by the "fit point" method ("noise band" 6.00; "treshold" 3.00), the sensitivity remained the same and the results for the calculated DNA concentrations were not falsified.

Figures 8A, 8B:
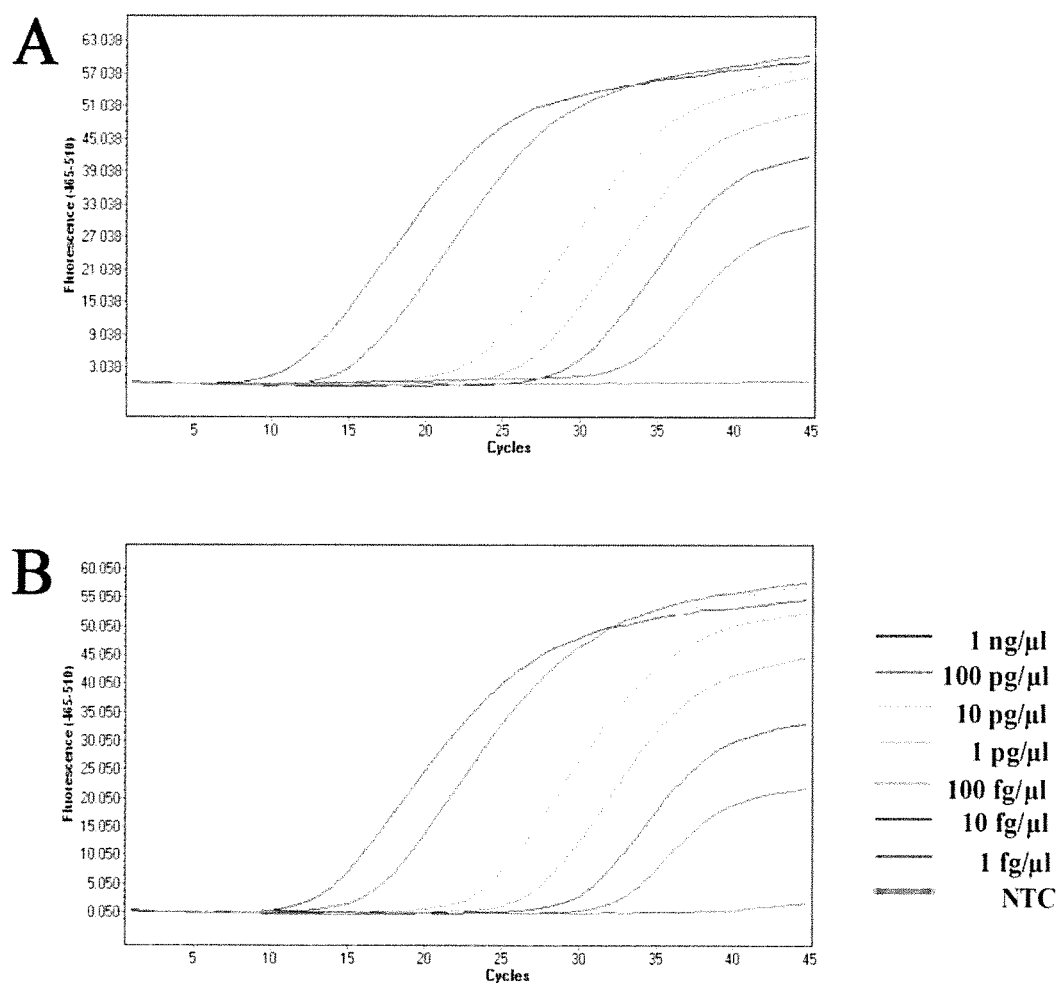

The stability or sensitivity of a PCR can be affected under field conditions when DNA is extracted from feces or tissue. The possible inhibitory action was ruled out by means of a plasmid DNA dilution series (1 ng/µl to 1 fg/µl) which had been treated with DNA from negative feces (FIG. 8).

Even when the reaction preparations of the dilution series of plasmid DNA with DNA from MAP-negative feces were submitted, the sensitivity remained the same and the result was not falsified. To illustrate the agreement of the calculated with the known MAP DNA concentrations, these were calculated and compared in Table 4.

TABLE 4

Calculated concentrations and found Cp values of plasmid DNA in $\log_{10}$ dilution stages (1 ng/µl to 1 fg/µl) by TaqMan real-time PCR.

| Sample | Known conc. | H$_2$O | | Fecal DNA | |
|---|---|---|---|---|---|
| | | Calculated conc. | Crossing point | Calculated conc. | Crossing point |
| 1 ng/µl | $10^{-9}$ | $9.63 \times 10^{-10}$ | 11.61 ± 0.07 | $9.97 \times 10^{-10}$ | 13.53 ± 0.12 |
| 100 pg/µl | $10^{-10}$ | $1.08 \times 10^{-10}$ | 15.27 ± 0.22 | $1.05 \times 10^{-10}$ | 16.88 ± 0.02 |
| 10 pg/µl | $10^{-11}$ | $9.67 \times 10^{-12}$ | 19.22 ± 0.11 | $9.42 \times 10^{-12}$ | 20.47 ± 0.14 |
| 1 pg/µl | $10^{-12}$ | $7.51 \times 10^{-13}$ | 23.33 ± 0.24 | $9.89 \times 10^{-13}$ | 23.83 ± 0.03 |
| 100 fg/µl | $10^{-13}$ | $9.00 \times 10^{-14}$ | 26.63 ± 0.15 | $1.03 \times 10^{-13}$ | 27.20 ± 0.07 |
| 10 fg/µl | $10^{-14}$ | $1.14 \times 10^{-14}$ | 29.75 ± 0.06 | $9.83 \times 10^{-15}$ | 30.13 ± 0.17 |
| 1 fg/µl | $10^{-15}$ | $9.85 \times 10^{-16}$ | 33.33 ± 0.07 | $1.01 \times 10^{-15}$ | 32.34 ± 0.03 |
| NTC | — | — | — | — | — |

In spite of mixing with DNA from MAP-negative feces, no serious shifts in the values are discernible. Similar values of the known and calculated DNA concentrations indicate the basic usability of TaqMan real-time PCR for quantifying MAP DNA irrespective of the matrix feces.

Figure 9:
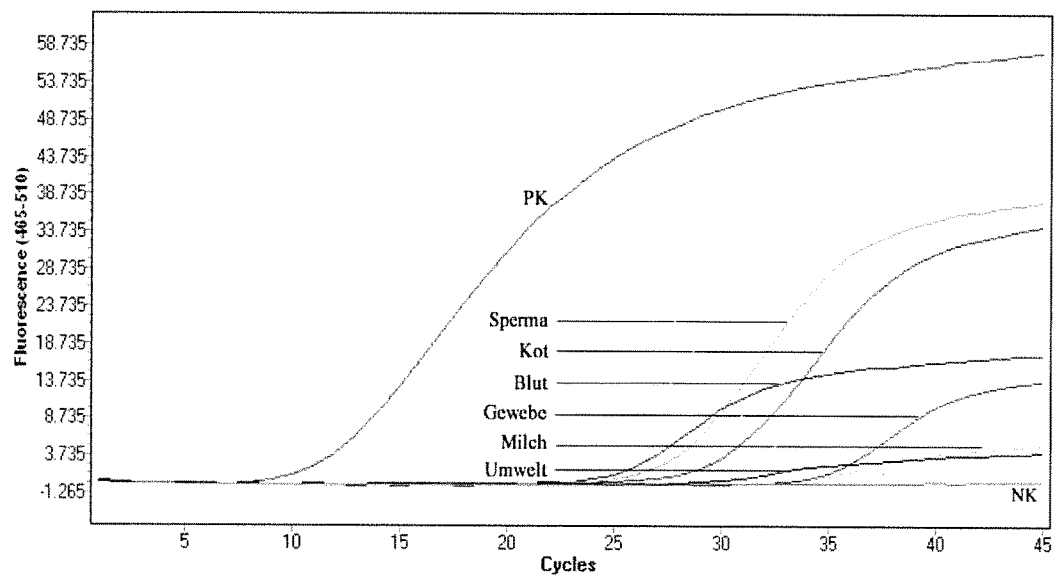

For wide applicability of the real-time PCR in routine diagnosis and in research, the detection of MAP DNA in different matrices must be ensured. In order to support its universal use, samples taken from the routine diagnosis archive and which have already tested positive in the "semi-nested" PCR were tested twice on the LightCycler™ 480. Fecal, milk, semen, blood, tissue and environmental samples were selected (FIG. 9).

MAP DNA could be reliably detected in all matrices in both runs. The Cp values for both runs and the mean values and standard deviation are shown in Table 5.

TABLE 5

Found Cp values for the different matrices on the LightCycler ™ 480 with the TaqMan probe.

|  | Feces | Milk | Semen | Blood | Tissue | Environment |
|---|---|---|---|---|---|---|
| Run 1 | 25.07 | 33.53 | 27.83 | 30.00 | 33.26 | 29.33 |
| Run 2 | 26.28 | 33.34 | 27.85 | 29.97 | 31.88 | 29.30 |
| Mean | 25.68 ± | 33.44 ± | 27.84 ± | 29.99 ± | 32.57 ± | 29.32 ± |
| S.D. | 0.86 | 0.13 | 0.01 | 0.02 | 0.98 | 0.02 |

The fecal, milk, semen, blood, tissue and environmental samples tested gave a clear fluorescent signal with Cp values between 25.07 and 33.53. The result was reproducible with standard deviations of 0.02 to 0.98.

For the use of real-time PCR for the detection of *paratuberculosis* in ruminants, control systems for amplification (for example HEX channel) or extraction (for example Cy5 channel) which can be independently detected over other labels or markers can be used. At the same time, successful nucleic acid extraction can be detected for example by amplification of the target gene β-actin. Further control systems for amplification or extraction are known to those skilled in the art.

The final protocol for the MAP TaqMan real-time PCR is as follows:

| 95° C. | 10 mins |  |
|---|---|---|
| 95° C. | 15 secs |  |
| 60° C. | 30 secs | 40 cycles |
| 72° C. | 35 secs |  |

On analysis with a control system for amplification and extraction in the FAM channel (465-510 nm), the samples taken from the archive also gave a reproducible clear fluorescent signal with average Cp values between 23.58 and 33.29 and standard deviations of 0.02 to 0.98.

The test described was evaluated with 13 cattle which had tested positive for MAP. For this, DNA was extracted from the fecal samples and tested for MAP with the real-time PCR described. Here it was found that the test could detect MAP in fecal samples.

Finally, to confirm the robustness of the test, organ samples from different intestinal areas of two cows were tested. As can be seen from the tables below, the test according to the invention is suitable for the detection of MAP.

TABLE 7

Quantitative use of the IS900 TagMan real-time PCR for detection of MAP in tissue samples from two cows suffering from paratuberculosis. Cp values measured three times in the FAM channel (465-510 nm) are shown.

| Animal | Sample | FAM channel (465-510 nm) |
|---|---|---|
| Animal A | Duodenum | 32.68 ± 0.21 |
|  | Jejunum | 28.00 ± 0.12 |
|  | Ileum | 27.09 ± 0.08 |
|  | Caecum | 25.06 ± 0.04 |
|  | Ln caecalis | 33.00 ± 0.23 |
| Animal B | Duodenum | 33.79 ± 0.69 |
|  | Jejunum | 34.33 ± 0.61 |
|  | Ileum | 25.52 ± 0.03 |
|  | Caecum | 24.53 ± 0.03 |
|  | Ln caecalis | 28.86 ± 0.11 |

All samples showed an amplification curve in the FAM channel with Cp values of 24.53 to 34.33 and standard deviations of 0.03 to 0.69.

Figure 10:
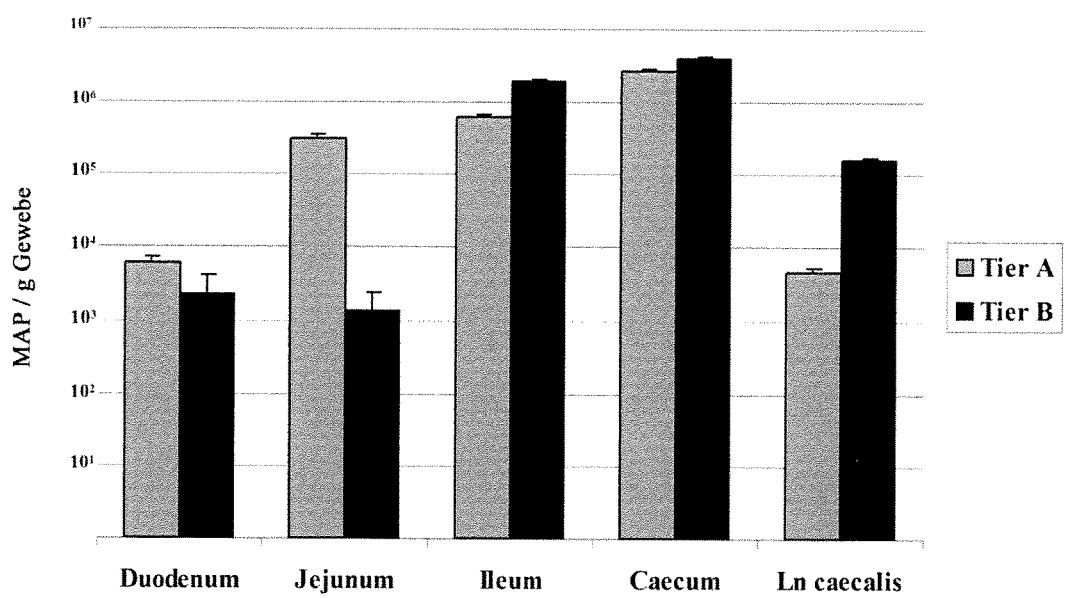

For a quantitative assessment, as already described above, DNA concentration and MAP genome units per gram of tissue were calculated (Table 8) and presented in graph form (FIG. 10).

TABLE 8

Quantitative use of the IS900 TaqMan real-time PCR for the detection of MAP in tissue samples from two cows suffering from paratuberculosis. For quantification of MAP in tissue, the DNA concentration and the number of genome units per gram of tissue were calculated.

| Animal | Sample | DNA concentration | MAP/g tissue |
|---|---|---|---|
| Animal A | Duodenum | $7.99 \times 10^{-14}$ | $6.21 \times 10^3$ |
|  | Jejunum | $4.04 \times 10^{-12}$ | $3.14 \times 10^5$ |
|  | Ileum | $8.13 \times 10^{-12}$ | $6.32 \times 10^5$ |
|  | Caecum | $3.57 \times 10^{-11}$ | $2.77 \times 10^6$ |
|  | Ln caecalis | $5.96 \times 10^{-14}$ | $4.63 \times 10^3$ |
| Animal B | Duodenum | $3.27 \times 10^{-14}$ | $2.54 \times 10^3$ |
|  | Jejunum | $1.91 \times 10^{-14}$ | $1.48 \times 10^3$ |
|  | Ileum | $2.57 \times 10^{-11}$ | $2.00 \times 10^6$ |
|  | Caecum | $5.17 \times 10^{-11}$ | $4.02 \times 10^6$ |
|  | Ln caecalis | $2.05 \times 10^{-12}$ | $1.59 \times 10^5$ |

In a validation study, the commercially available MAP PCR kits Adiavet (Adiavet Para™ Realtime), AB-TaqMan (Applied Biosystems Taq-ManMAP) and Vetmax (Applied Biosystems VetMax MAP Real Time PCR Screening Kit), and a PCR assay published in Bull et al. (Tim J. Bull et al., 2007, Plos One 2007(11), e1229) were tested in comparison to the real-time PCR described here. With the commercially available kits, this was performed according to the manufacturers' instructions. As the reference, a semi-nested PCR (snPCR) was used (Münster P. et al., Vet Microbiol. 2011: 154(1-2): 197-201). With the detection of 1 genome unit, it has the highest sensitivity and is superior to all "real-time" methods as regards sensitivity. However, it is the general state of the art that such snPCRs are unsuitable for routine applications because of the extremely high contamination risk with mass throughput.

The PCR runs took place on a Roche LightCycler 480. The snPCR ran in the standard way on a conventional Thermocycler (Biometra "Trio").

As test samples, 14 fecal samples tested negative by semi-nested PCR (snPCR) and 35 tested positive from routine diagnosis (n=49) were available.

The test results are summarized in Table 9 for the fecal samples which tested positive. The Cp values from two tests were averaged. If the results from only one test were available, these were used for the further analyses. The validation in Table 9 shows the difference between the Cp values. Firstly the TaqMan real-time PCR was tested against all commercially available comparison PCRs. For this, in each case the corresponding "comparison PCR samples Cp value" was subtracted from the relevant "TaqMan PCR samples Cp value". A positive value in the relevant column indicates that the TaqMan PCR Cp value was higher than the subtracted comparison value. Accordingly the PCR was poorer in sensitivity than the comparison PCR, since by definition the lower the Cp value is, the higher the sensitivity. Similarly, a comparison was made between the TaqMan PCR and the published PCR of Bull et al., in which the end volume in the TaqMan real-time PCR was matched to the PCR described by Bull et al. (50 μl each instead of 20 μl).

The comparison study comes to the conclusion that the newly developed PCR was superior to all comparison PCRs. [The TaqMan real-time PCR Plus in the classical version (5 μl template) beat all comparison PCRs. It was also just superior to a modification of itself with 8 μl template].

TABLE 9

Results of the validation study

| Serial No. | snPCR | TaqMan Adiavet | TaqMan ABTaqMan | TaqMan Vetmax | TaqMan Bull et al. |
|---|---|---|---|---|---|
| 1 | + | −7.55 | −2.92 | −2.06 | −5.31 |
| 2 | + | 7.44 | −2.91 | −2.00 | −5.59 |
| 3 | + | −2.73 | −1.54 | −1.02 | −4.62 |
| 4 | + | −2.67 | −1.23 | −0.79 | −4.30 |
| 5 | + | −6.95 | −2.42 | −1.23 | −4.57 |
| 6 | + | 3.65 | −1.61 | −0.47 | −3.37 |
| 7 | + | −10.07 | −1.39 | 0.74 | −2.32 |
| 8 | + | −6.49 | −2.31 | −1.37 | −4.44 |
| 9 | + | −7.95 | −8.10 | −10.97 | −4.89 |
| 10 | + | 2.19 | −1.82 | −6.31 | −0.27 |
| 11 | + | −4.85 | −10.82 | −13.86 | −8.96 |
| 12 | + | 2.56 | −7.86 | −13.82 | −7.72 |
| 13 | + | −9.21 | −9.43 | −12.34 | −3.61 |
| 14 | ++ | 0.41 | 2.75 | 1.73 | −2.59 |
| 15 | ++ | −3.85 | −0.28 | −1.40 | −4.75 |
| 16 | + | −11.20 | −11.20 | −11.20 | −4.39 |
| 17 | + | −11.95 | −11.95 | −11.95 | −4.36 |
| 18 | + | 3.59 | 9.85 | 8.76 | 5.59 |
| 19 | + | 10.11 | −10.11 | −10.11 | −2.92 |
| 20 | + | −12.24 | −12.24 | −12.24 | −5.77 |
| 21 | + | −12.34 | −13.03 | −13.03 | −3.17 |
| 22 | + | −6.48 | −6.48 | −6.48 | −6.48 |
| 23 | + | 0.00 | 8.07 | 6.93 | 4.29 |
| 24 | + | 2.94 | 2.81 | 0.00 | 0.73 |
| 25 | + | −8.91 | −9.15 | −11.62 | −9.78 |
| 26 | + | 0.00 | 0.00 | 0.00 | 5.98 |
| 27 | + | 3.05 | 2.88 | 0.00 | 5.21 |
| 28 | + | −12.30 | −12.30 | −12.30 | −4.65 |
| 29 | + | 0.00 | 0.00 | 0.00 | 1.63 |
| 30 | + | 0.00 | 0.00 | 0.00 | 1.91 |
| 31 | + | −13.52 | −13.52 | −13.52 | / |

TABLE 9-continued

Results of the validation study

| Serial No. | snPCR | TaqMan Adiavet | TaqMan ABTaqMan | TaqMan Vetmax | TaqMan Bull et al. |
|---|---|---|---|---|---|
| 32 | + | −11.59 | −11.59 | −11.59 | / |
| 33 | + | −10.40 | −10.40 | −10.40 | −10.40 |
| 34 | + | 0.00 | 0.00 | 0.00 | 0.00 |
| 35 | + | 0.00 | 0.00 | 0.00 | 0.00 |
| | better | 25/35 | 25/35 | 24/35 | 24/33 |
| | same | 6/35 | 5/35 | 7/35 | 2/33 |
| | worse | 4/35 | 5/35 | 4/35 | 7/33 |

The above comparison clearly shows that the method according to the invention with the primers according to the invention is superior in sensitivity to the methods described in the state of the art and the commercially available test kits.

BRIEF DESCRIPTION OF DIAGRAMS

FIG. 1: Graphical representation of the primers used ($MAP_{523-542f}$/$Map_{661-642r}$) and patents for IS 900.

FIG. 2: Specificity clarification for the primers ($MAP_{523-542f}$/$Map_{661-642r}$) with non-*mycobacterial* species. For this, amplified PCR products were separated by gel electrophoresis (1.5% agarose gel).

FIG. 3: Specificity determination of the TaqMan real-time PCR on the LightCycler™ 480 on the basis of reference strains (n=14).

FIG. 4: Specificity clarification for the primers ($MAP_{523-542f}$/$Map_{661-642r}$) with other *mycobacterium* species. For this, amplified PCR products were separated by gel electrophoresis (1.5% agarose gel).

FIG. 5: Sensitivity determination of the real-time PCR on the basis of ATCC 19698 MAP DNA. A: 1 ng/μl, B: 100 pg/μl, C: 10 pg/μl, D: 1 pg/μl, E: 100 fg/μl, F: 10 fg/μl, G: 1 fg/μl, NTC: sterile water.

FIG. 6: Reproducibility of the TaqMan real-time PCR on the basis of 9 repetitions (3×3 runs) (efficiency=1.97±0.08; error=0.04±0.02). Evaluation was by the "$2^{nd}$ derivative maximum" method.

FIG. 7: Reproducibility of the TaqMan real-time PCR on the basis of 9 repetitions (3×3 runs) (efficiency=2.07±0.09; error=0.18±0.03). Evaluation was by the "fit point" method.

FIG. 8: Graphical representation of the amplification curves of the plasmid DNA dilution series (1 ng/μl to 1 fg/μl) mixed with $H_2O$ (A) and fecal DNA (B) on the LightCycler™ 480 with a TaqMan probe. Curves from L to R: 1 ng/μl, 100 pg/μl, 10 pg/μl, 1 pg/μl, 100 fg/μl, 10 fg/μl, 1 fg/μl, sterile water (NTC).

FIG. 9: Graphical representation of the amplification curves for detection of MAP DNA from various matrices on the LightCycler™ 480 with a TaqMan probe.

FIG. 10: Quantitative use of the IS900 TaqMan real-time PCR for detection of MAP in tissue samples. Comparison of animal A and animal B. The bars represent the mean value and the standard deviation (3 repetitions) of the calculated MAP concentration in various tissues.

The invention claimed is:

1. A method for specific detection and optionally quantification of *Mycobacterium avium* spp. *para-tuberculosis* (MAP) in a sample comprising the steps of:
   providing specific oligonucleotides respectively consisting of the sequences according to SEQ ID NO: 1 and SEQ ID NO: 2;
   performing a real-time polymerase chain reaction (PCR) with said specific oligonucleotides and a probe according to SEQ ID NO: 3 and having a fluorophore label; and
   detecting the IS900 region of a MAP genome in a sample wherein detection of the IS900 region of at least one MAP genome indicates the presence of MAP,
   wherein the specific detection of MAP is effected by real-time PCR and use of the specific oligonucleotides and the probe.

2. The method for specific detection of MAP as claimed in claim 1 wherein the detection is effected as quantitative real-time PCR.

3. The method as claimed in claim 1, wherein the sample is one of fecal, milk, blood, semen, tissue, organ and environmental samples.

4. The method as claimed in claim 1, wherein the sample derives from ruminants or humans.

5. The method of claim 4, wherein the sample is derived from cattle, sheep, or goats.

6. A composition for specific detection and, optionally, for quantification of MAP in a sample from an individual, comprising oligonucleotides wherein the oligonucleotides consist of the oligonucleotides according to SEQ ID NO: 1, SEQ ID NO: 2 and SEQ ID NO: 3, wherein the oligonucleotide according to SEQ ID NO: 3 is labelled with a fluorophore.

* * * * *